United States Patent [19]

Conta et al.

[11] Patent Number: 4,606,343
[45] Date of Patent: Aug. 19, 1986

[54] SELF-POWERED SURGICAL FASTENING INSTRUMENT

[75] Inventors: Robert L. Conta; Harvey N. Wallach, both of Trumbull, Conn.

[73] Assignee: United States Surgical Corporation, Norwalk, Conn.

[21] Appl. No.: 177,231

[22] Filed: Aug. 18, 1980

[51] Int. Cl.$^4$ .................. A61B 17/04; A61B 17/32
[52] U.S. Cl. ................. 128/305; 128/334 R; 227/DIG. 1
[58] Field of Search ............ 128/334 R, 325; 227/19, 227/DIG. 1

[56] References Cited

U.S. PATENT DOCUMENTS

| | | | |
|---|---|---|---|
| 4,705 | 8/1846 | Tiemann | 128/315 |
| 3,193,165 | 7/1965 | Akhalaya et al. | 227/8 |
| 3,388,847 | 6/1968 | Kasulin et al. | 227/19 |
| 3,552,626 | 1/1971 | Astafiev et al. | 227/76 |
| 3,593,903 | 7/1971 | Astafiev et al. | 227/76 |
| 3,790,057 | 2/1974 | Razgulov et al. | 227/19 |
| 3,837,555 | 9/1974 | Green | 227/130 |
| 4,203,446 | 5/1980 | Hofert et al. | 128/329 R |
| 4,207,898 | 6/1980 | Becht | 128/305 |

FOREIGN PATENT DOCUMENTS

| | | |
|---|---|---|
| 1057729 | 5/1959 | Fed. Rep. of Germany . |
| 587678 | 1/1959 | Italy . |
| 1241577 | 8/1971 | United Kingdom . |
| 119309 | 4/1958 | U.S.S.R. ............ 128/329 R |

OTHER PUBLICATIONS

Brochure of YUFU Medical, Inc. showing curved instruments for esophago-gastro anastomosis, prior to 2/8/79.
Japanese brochure showing straight instrument apparently for gastro-intestinal anastomosis.
"Information Booklet for Auto Suture® Model EEA Surgical Stapling Instrument and Disposable Loading Units", U.S. Surgical Corp., 1/79.

Primary Examiner—Michael H. Thaler
Attorney, Agent, or Firm—Thomas R. Bremer

[57] ABSTRACT

An instrument and method for performing a surgical fastening procedure at a location remote from the location at which the instrument is manipulated. The instrument is at least partly self-powered by self-powering apparatus (e.g., a prestressed spring) adjacent the location at which the fastening procedure is performed, the self-powering apparatus being controlled from the location at which the instrument is manipulated. The relatively large forces required for the surgical fastening procedure are confined to a relatively small portion of the instrument adjacent the location at which the fastening procedure is performed, thereby reducing the cost of the instrument as a whole and making it economical to provide as a disposable item.

24 Claims, 21 Drawing Figures

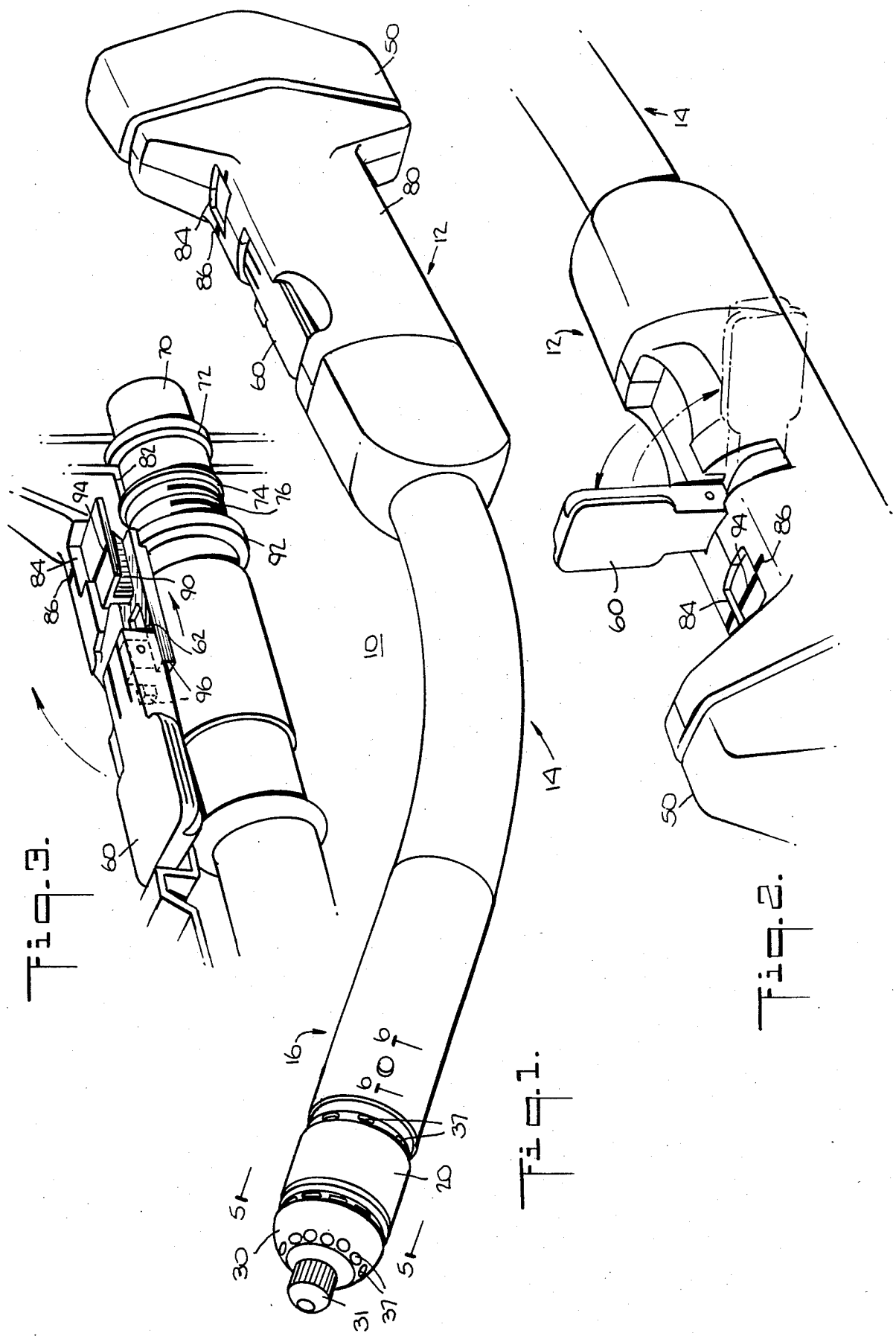

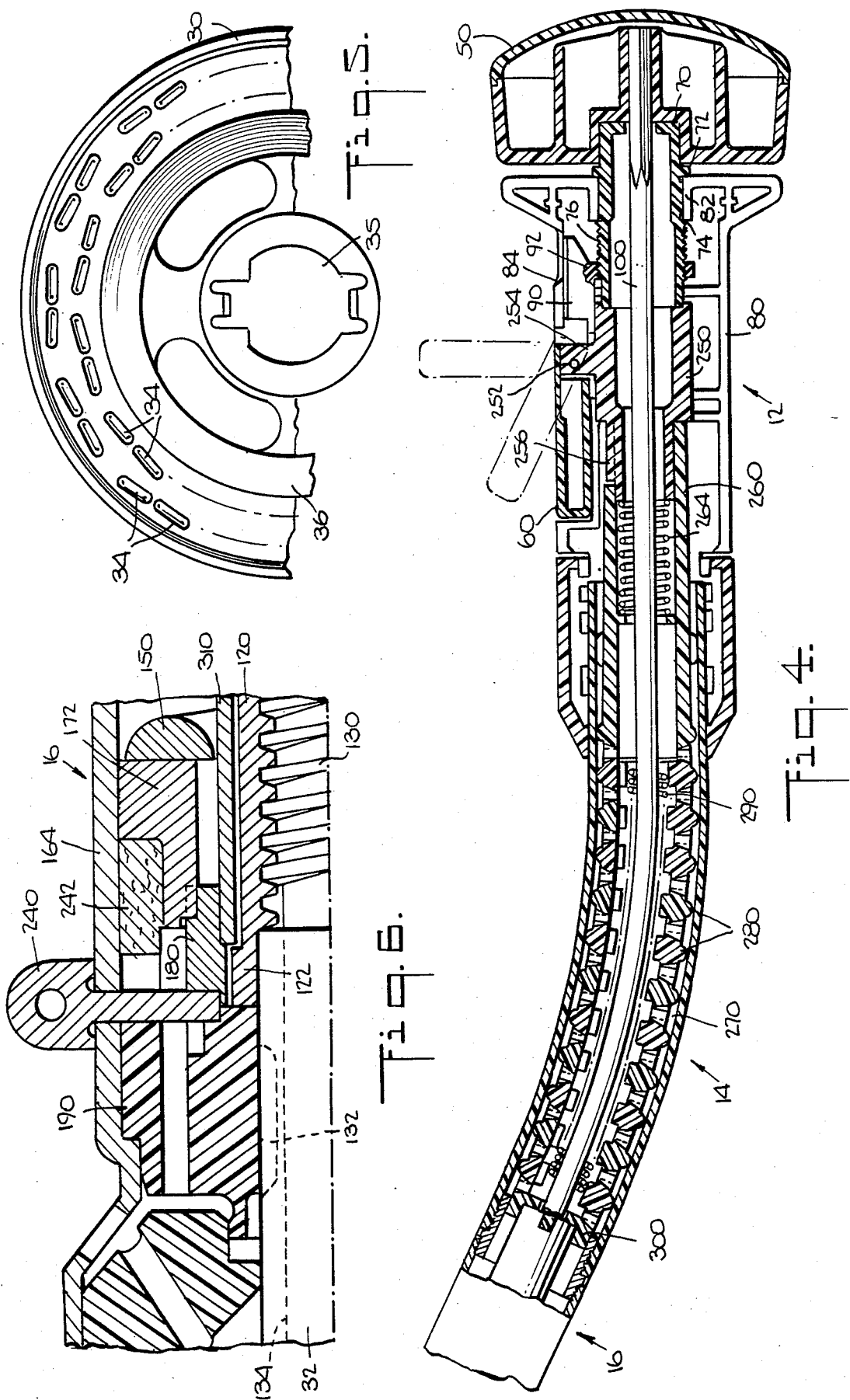

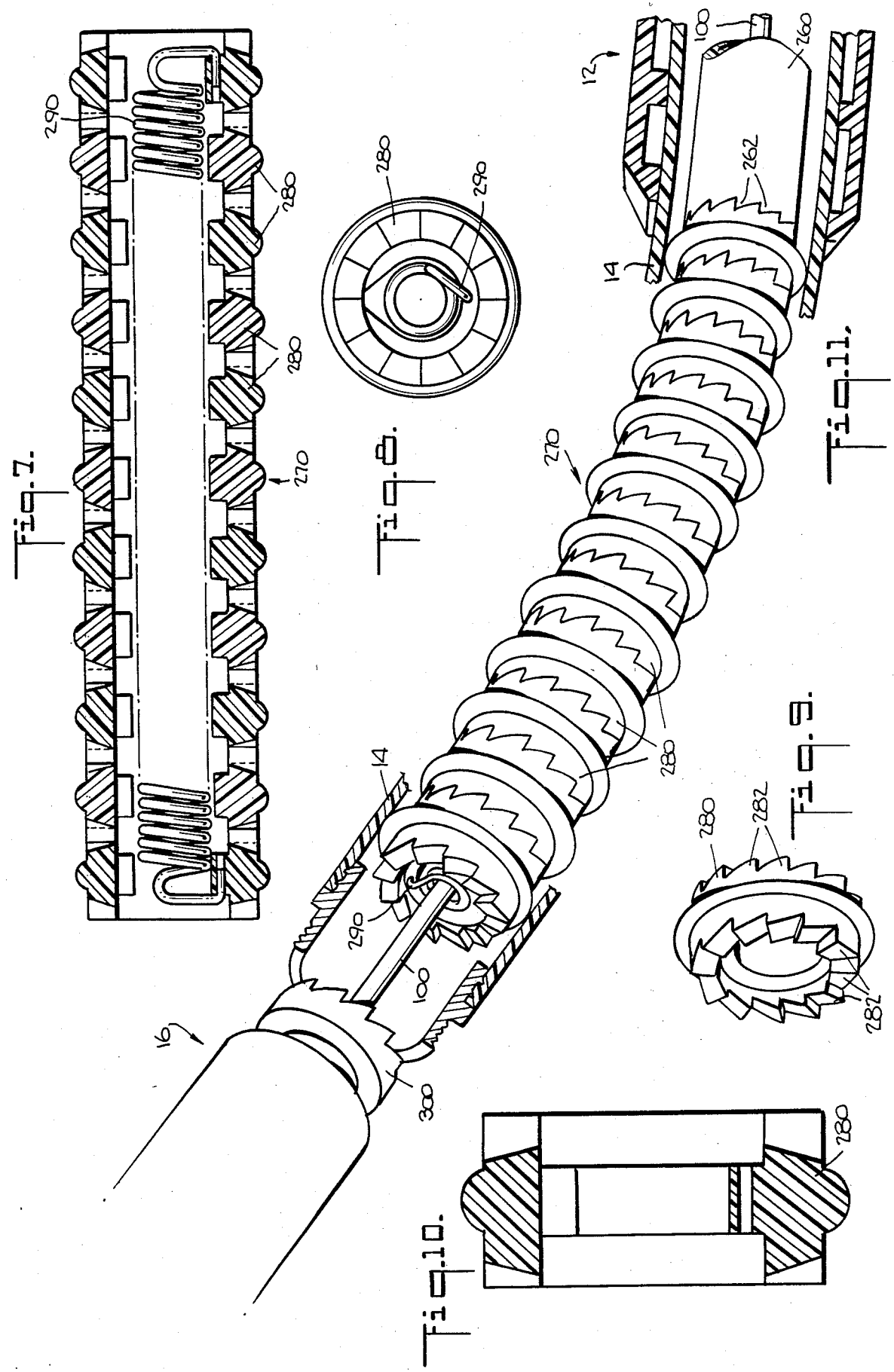

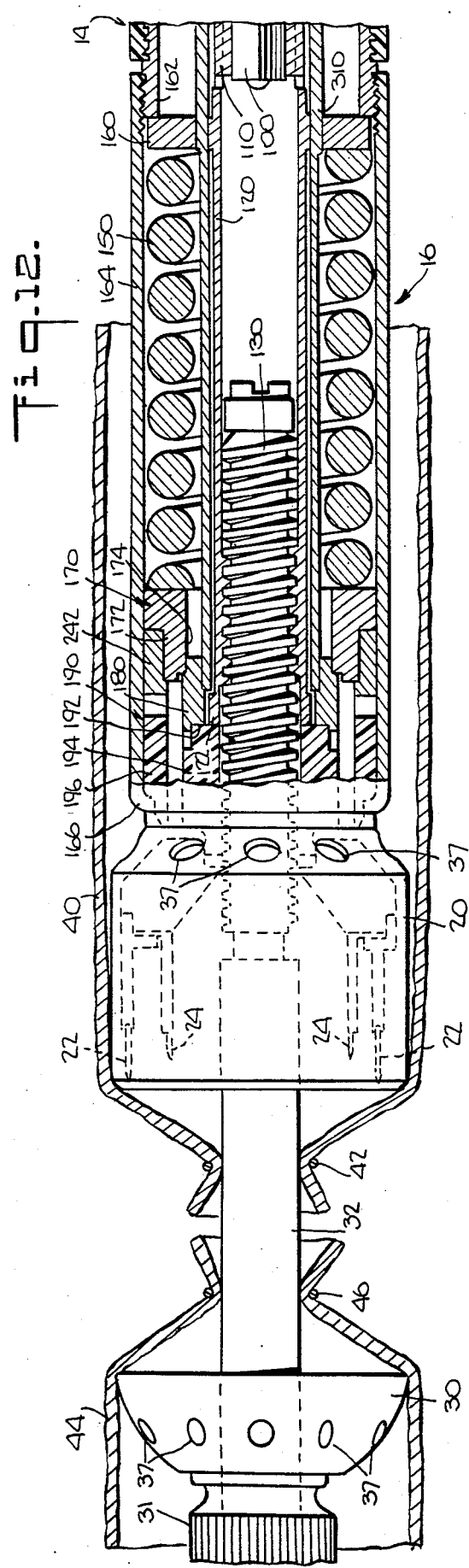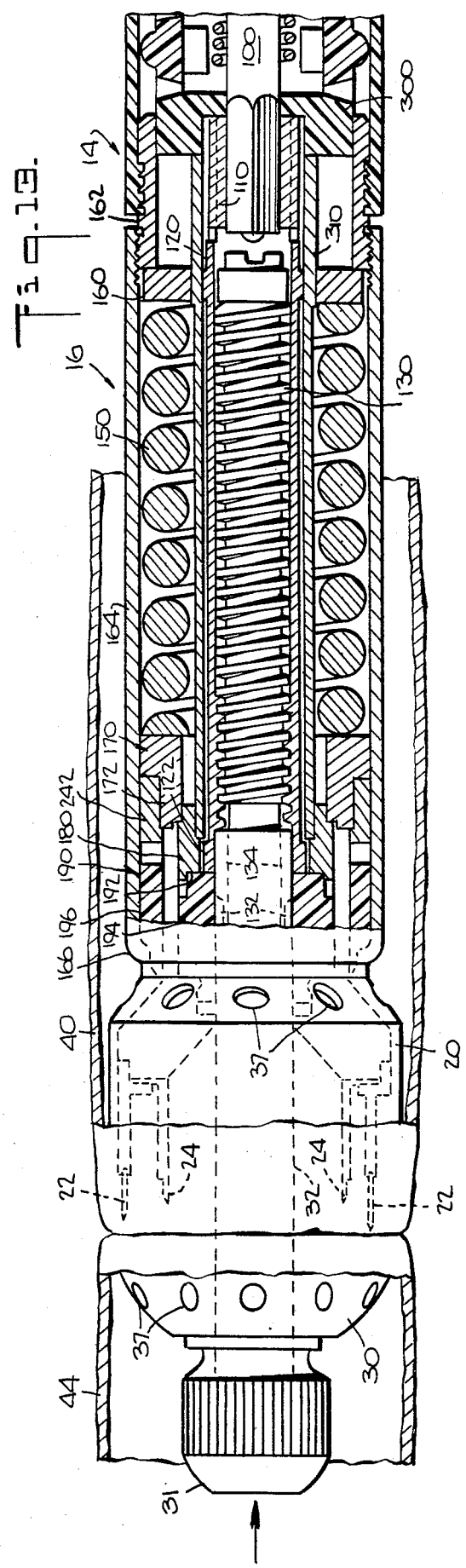

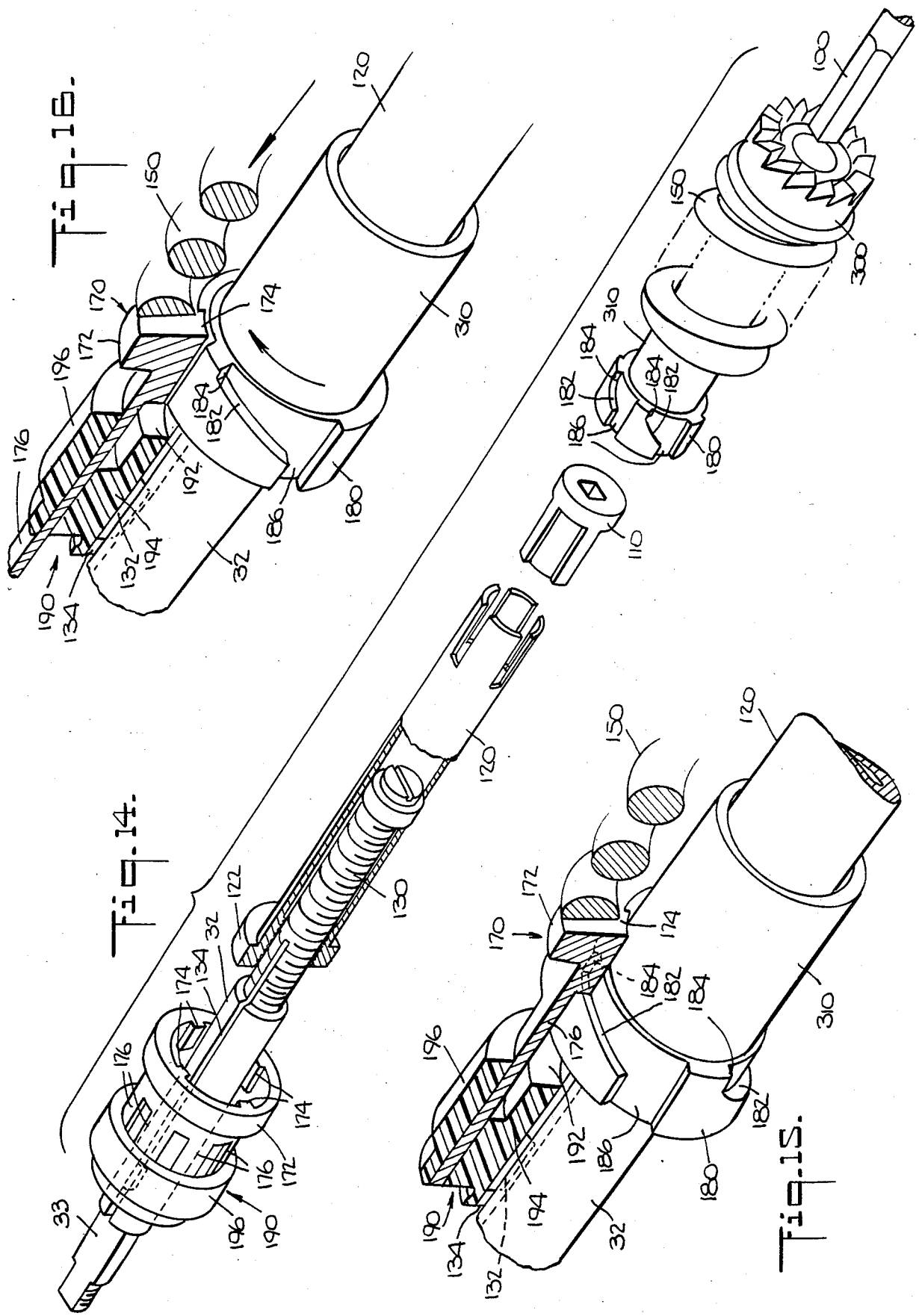

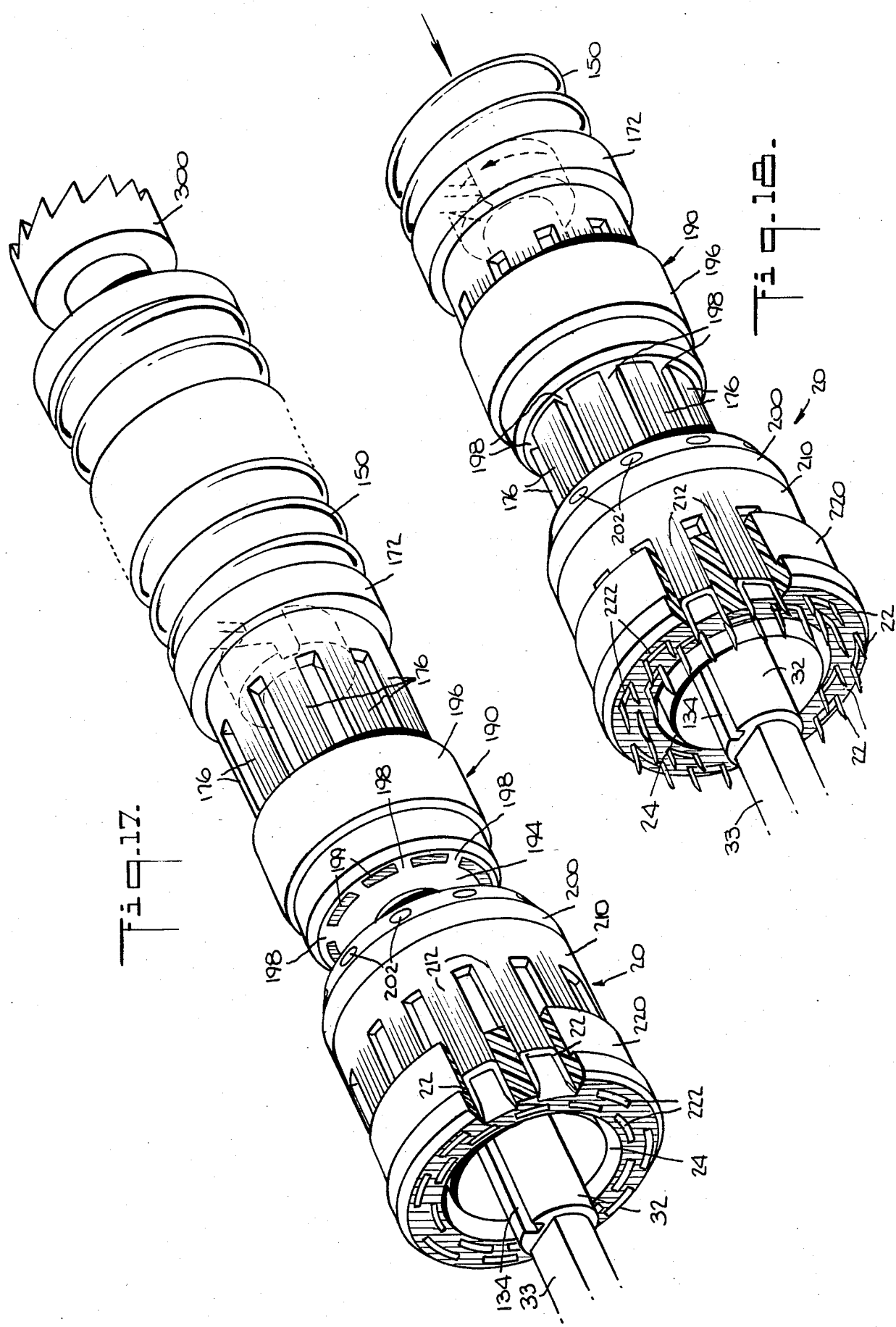

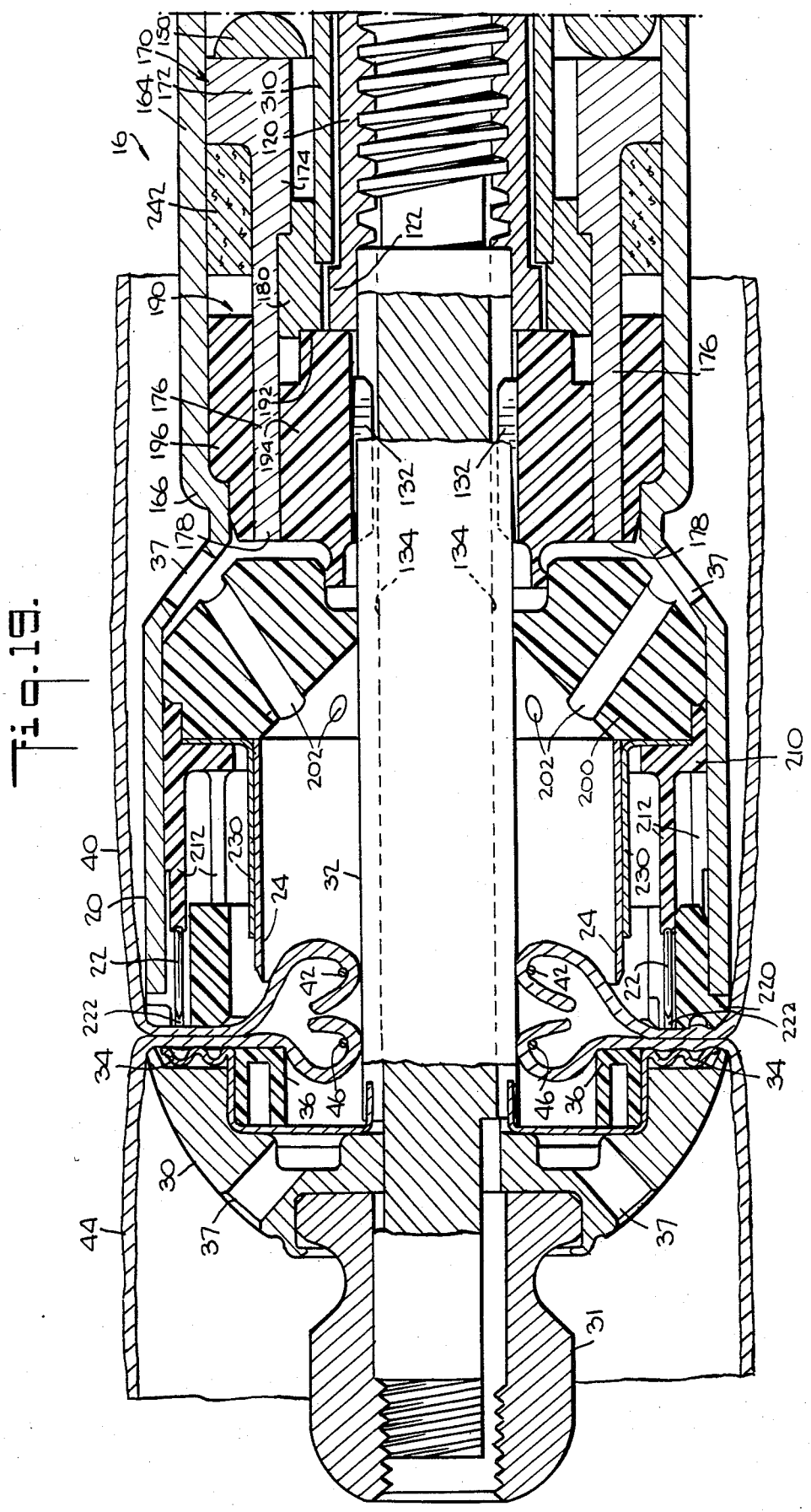

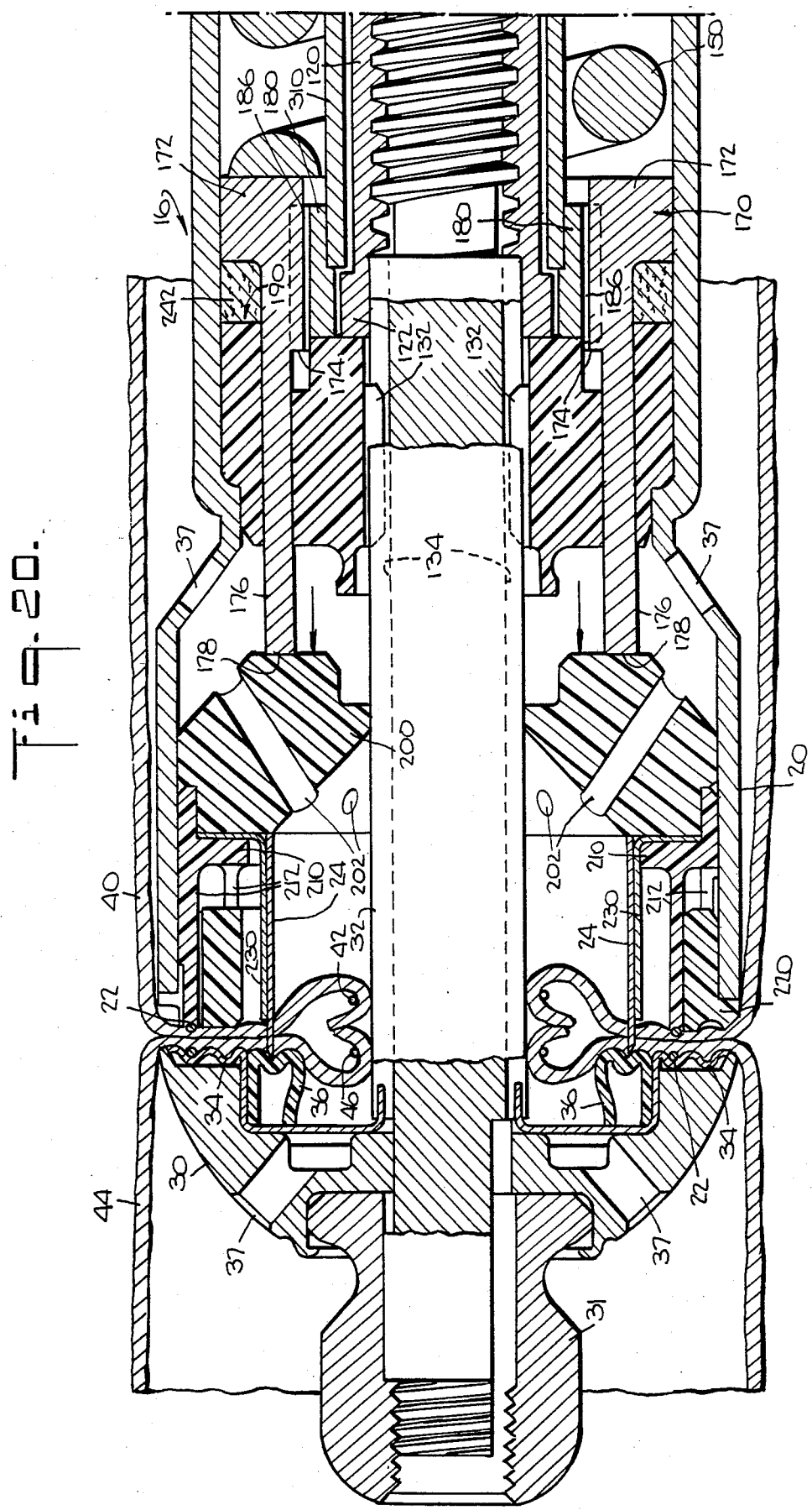

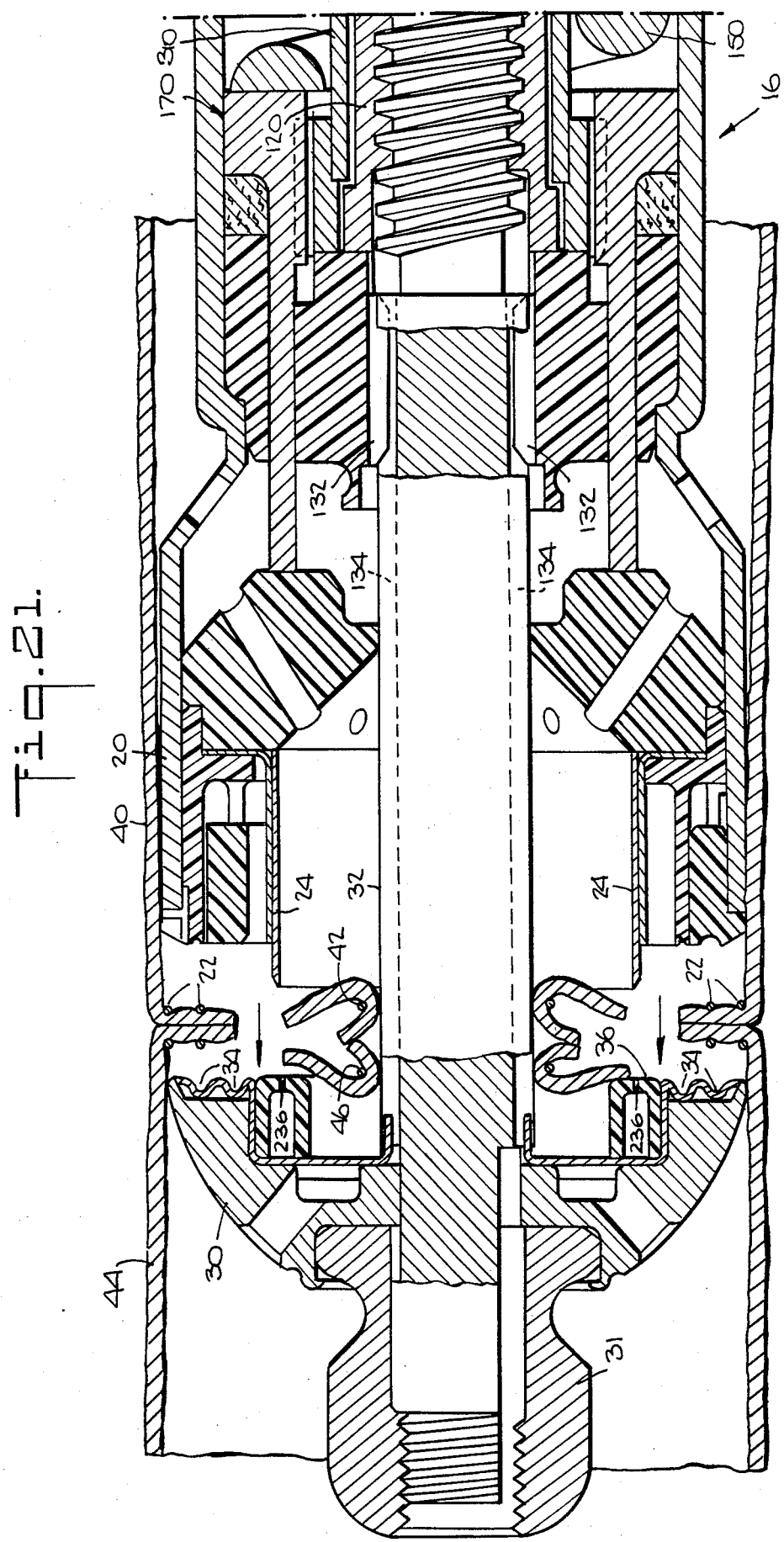

SELF-POWERED SURGICAL FASTENING INSTRUMENT

BACKGROUND OF THE INVENTION

This invention relates to surgical fastening instruments and methods, and more particularly to surgical fastening (e.g., surgical stapling) instruments and methods which are at least partly self-powered.

There is increasing interest in surgical fastening instruments such as surgical staplers which are self-powered, or at least partly self-powered. To the extent that such an instrument is self-powered, it saves work and time, produces results which are less subject to variation from user to user, and can be made less subject to variation from faulty use. Many surgical fastening procedures, however, require the application of considerable force, and it is difficult to store the energy required to develop such force in an instrument which typically must be relatively small.

It is therefore an object of this invention to improve and simplify surgical fastening instruments and methods, particularly those which are at least partly self-powered.

There is also increasing interest in surgical fastening instrument which are disposable after use in a single surgical procedure. This avoids the considerable expense of cleaning and sterilizing the instrument between uses. Again, however, it may be difficult or impossible to develop the relatively large forces required in many surgical fastening procedures using instruments made of the relatively inexpensive materials and having the lightweight construction typically required to make the instrument economically disposable. This is particularly a problem where the large forces must be applied at a location remote from the location at which the instrument is manipulated.

It is therefore another object of this invention to provide surgical fastening instruments which are at least partly self-powered, are capable of developing relatively large forces, and are economically disposable.

SUMMARY OF THE INVENTION

These and other objects of the invention are accomplished in accordance with the principles of the invention by providing a surgical fastening instrument which is at least partly powered by a compact self-powering mechanism disposed immediately adjacent the location at which the relatively large forces developed by the self-powering mechanism are required. The self-powering mechanism is controlled by relatively small control forces from the location at which the instrument is manipulated. The relatively large forces developed by the self-powering mechanism are thus confined to a relatively small portion of the instrument. The remaining major portion of the instrument is not subjected to these large forces and can therefore be made of relatively inexpensive materials in relatively light construction, thereby substantially reducing the cost of the instrument and making it economically disposable.

A surgical fastening procedure is performed in accordance with the method of the invention by positioning the instrument relative to the tissue on which the procedure is to be performed, operating the control or controls of the instrument to cause the various portions of the procedure to be performed including release of the self-powering mechanism, and removing the instrument from the tissue.

Further features of the invention, its nature and various advantages will be more apparent from the accompanying drawing and the following detailed description of the invention.

BRIEF DESCRIPTION OF THE DRAWING

FIG. 1 is an overall perspective view of an illustrative surgical fastening instrument constructed in accordance with the principles of the invention.

FIG. 2 is an enlarged perspective view of a portion of the instrument shown in FIG. 1.

FIG. 3 is another enarged perspective view of a portion of the instrument shown in FIG. 1, with a portion of the housing removed.

FIG. 4 is a longitudinal sectional view of a portion of the instrument shown in FIG. 1.

FIG. 5 is a partial cross sectional view taken along the line 5—5 in FIG. 1.

FIG. 6 is a longitudinal sectional view taken along the line 6—6 in FIG. 1.

FIG. 7 is an enlarged sectional view of a portion of the apparatus shown in FIG. 4.

FIG. 8 is an end view of the apparatus shown in FIG. 7.

FIG. 9 is a perspective view of one element in the apparatus shown in FIGS. 7 and 8.

FIG. 10 is a further enlarged sectional view of one element in the apparatus shown in FIGS. 7 and 8.

FIG. 11 is a partly exploded, partly sectional perspective view of a portion of the apparatus shown in FIG. 4.

FIG. 12 is a longitudinal sectional view of another portion of the instrument shown in FIG. 1, illustrating one step in the use of the instrument in accordance with the invention.

FIG. 13 is similar to FIG. 12, but illustrates a subsequent step in the use of the instrument.

FIG. 14 is an exploded perspective view, partly in section, showing a portion of the apparatus shown in FIGS. 12 and 13.

FIG. 15 is a partly sectional perspective view of a portion of the apparatus shown in FIGS. 12-14 showing the condition of the self-powering mechanism prior to release.

FIG. 16 is similar to FIG. 15 but shows the condition of the self-powering mechanism during release.

FIG. 17 is a partly exploded, partly sectional perspective view of a portion of the apparatus shown in FIGS. 12 and 13 showing that apparatus in a condition corresponding to the condition shown in FIG. 15.

FIG. 18 is similar to FIG. 17 but shows a condition corresponding to the condition shown in FIG. 16.

FIG. 19 is an enlarged longitudinal sectional view of a portion of the apparatus shown in FIG. 13 in the same condition as shown in that Figure.

FIGS. 20 and 21 are similar to FIG. 19 but show successive steps in the operation of the instrument.

DETAILED DESCRIPTION OF THE INVENTION

Although the principles of the invention are applicable to other surgical fastening instruments, the invention will be fully understood from an explanation of its application to a surgical stapler for performing anastomosis of holow body organs.

I. Overall Construction and Operation

As shown in FIG. 1, instrument 10 includes a handle portion 12 at the proximal end of an elongated hollow cylindrical tube or shaft 14. At the opposite distal end of shaft 14 is an assembly 16 in which the forces required to perform the anastomosis are produced. The anastomosis is actually performed between staple containing assembly 20 and anvil assembly 30 which are located at the distal end of force producing assembly 16. Instrument 10 is particularly adapted for performing end-to-end anastomosis of the large intestine using the rectal approach. Shaft 14 is therefore preferably curved as shown to facilitate positioning of the instrument during a procedure of this kind. The instrument is manipulated and controlled primarily by means of handle 12 outside the patient, while the anastomosis is actually performed by elements 20 and 30 at the distal end of the instrument.

The anastomosis procedure is best illustrated in FIGS. 12, 13, 19, 20, and 21, which show successive steps in the procedure. As shown for example in FIG. 12, staple containing assembly 20 initially contains a plurality of surgical staples 22 pointing toward anvil assembly 30 and arranged in two concentric annular rows (see also FIGS. 17 and 18). Staple containing assembly 20 also contains annular knife 24 concentric with but inside the annular staple array (see also FIGS. 17 and 18). Anvil assembly 30 is mounted opposite the distal end of staple containing assembly 20 on the end of rod 32. Anvil assembly 30 is held in place on the end of rod 32 by knurled nut 31, and (as shown in FIGS. 5 and 14) is prevented from rotating reative to rod 32 by co-operation of the flat-sided segment 33 of rod 32 and similarly shaped aperture 35 in anvil assembly 30. As best seen in FIG. 5, anvil assembly 30 has two concentric annular rows of staple crimping pockets 34 and annular knife anvil 36. Each staple pocket 34 is aligned with a respective one of staples 22, and knife anvil 36 is similarly aligned with knife 24. Anvil assembly 30 is movable axially toward and away from the distal end of staple containing assembly 20 by reciprocation of rod 32. Vents 37 in anvil assembly 30 and staple containing assembly 20 prevent fluid pressure from building up unduly in any part of the apparatus during any phase of the anastomosis procedure.

After the diseased tissue has been removed by conventional techniques, the anastomosis procedure begins as shown in FIG. 12 by inserting the distal end of instrument 10 through one section 40 of the tissue to be anastomosed (e.g., through the rectum in anastomosis of the large intestine using the rectal approach) so that only anvil assembly 30 extends beyond the end of tissue section 40. Anvil assembly 30 is separated from staple containing assembly 20 (if necessary) by operation of handle 12 as described below to expose a section of rod 32. The end of tissue 40 is tied around rod 32 by suture 42. The end of the other section 44 of tissue to be anastomosed is fitted over anvil assembly 30 and tied around rod 32 by suture 46. Handle 12 is then operated again as described below to bring anvil assembly 30 and staple containing assembly 20 together, thereby approximating the tissue to be anastomosed as shown in FIGS. 13 and 19.

Another portion of handle 12 is then operated as described below to release a self-powering mechanism (also described below) in assembly 16 to cause staples 22 to be driven through the approximated tissue and crimped by means of anvil pockets 34 as shown in FIG. 20. Knife 24 also advances as shown in FIG. 20 and cuts through the excess tissue inside the annular staple array.

Hande 12 is then operated again as described below to separate anvil assembly 30 from staple containing assembly 20 as shown in FIG. 21. Tissue sections 40 and 44 remain attached together (anastomosed) by means of staples 22, and the instrument can be withdrawn from tissue section 40. The excess tissue cut away by knife 24 remains tied around rod 32 and is removed with the instrument.

II. Construction and Operation of the Anvil Positioning Mechanism

Considering now the construction and operation of instrument 10 in more detail, and returning again to FIG. 1, handle 12 includes rotatable knob 50 on the proximal end of the handle for controlling the position of anvil assembly 30 relative to staple containing assembly 20. Handle 12 also includes control mechanism 60 for controlling the operation of the self-powering mechanism which drives staples 22 and knife 24 as mentioned above. Because in normal operation knob 50 is first operated to position anvil assembly 30, that portion of the apparatus will be described in detail before a detailed description of control mechanism 60 and its associated apparatus is given.

As shown for example in FIG. 4, knob 50 is mounled on the end of a short, hollow, cylindrical shaft 70 which is rotatably mounted in the end of handle body 80. Shaft 70 is prevented from moving axially relative to handle body 80 by annular shaft collars 72 and 74 in cooperation with annular bearing portion 82 of handle body 80. A portion 76 of shaft 70 inside handle body 80 is threadably engaged with indicator member 90 via threaded collar 92 (see also FIG. 3). Indicator member 90 is slidable longitudinally of handle body 80 to indicate the position of anvil assembly 30 relative to staple containing assembly 20 as will be described in more detail below.

Continuing with FIG. 4, the proximal end of flexible connection 100 is fitted into knob 50 so that flexible connection 100 rotates with knob 50. Flexible connection 100 may be any type of flexible mechanical connection (e.g., a cable of the type used in speedometers) which is capable of transmitting torque along its length. Flexible connection 100 extends through handle body 80 and coaxially through shaft 14. At the distal end of shaft 14, flexible connection 100 fits into rotatably mounted annular bushing 110 (see FIGS. 12-14). Bushing 110 engages hollow cylindrical shaft 120 which is rotatably mounted coaxially in assembly 16. Accordingly, the rotation of knob 50 is transmitted to shaft 120 via flexible connection 100 and bushing 110. Shaft 120 is prevented from moving axially by collar 122 which is located on the distal end of the shaft between collar 190 and the distal end of shaft 310.

As shown for example in FIGS. 12-14, shaft 120 is threaded internally to engage the threaded end 130 of rod 32. Anvil assembly 30 is mounted on the other end of rod 32 as described above. Rod 32 is axially movable relative to shaft 120, but is prevented from turning with shaft 120 by fixed keys 132 on collar 190 in cooperation with longitudinal keyways 134 in rod 32 (see aso FIG. 6). Accordingly, rod 32 moves anvil assembly 30 axially toward or away from staple containing assembly 20 when shaft 120 is rotated by knob 50. Anvil assembly 30 moves toward staple containing assembly 20 when knob 50 is rotated in one direction, and away from staple containing assembly 20 when knob 50 is rotated in the opposite direction. Because anvil assembly 30 cannot rotate relative to staple containing assembly 20, anvil staple pockets 34 always remain properly aligned with staples 22.

It should be noted that the force required to move and/or hold anvil assembly 30 relative to staple containing assembly 20 is developed largely in assembly 16 by the threaded connection between shaft 120 and rod 32. Because of the mechanical advantage of that connection, a relatively small torque in flexible connection 100 can produce a large force for moving assembly 30 as may be required, for example, to approximate and clamp the tissue lo be anastomosed. The tissue approximating and clamping force may be approximately 200–300 lbs.

Since it may be difficult or impossible for the user of the instrument to see or judge the spacing between staple containing assembly 20 and anvil assembly 30 when the instrument is in use, indicator member 90, mentioned above and shown in FIG. 1–4, provides a visible indication of this spacing at the proximal end of the instrument. Because of the threaded connection 76 and 92 between indicator member 90 and shaft 70, indicator member 90 moves axially of the instrument in proportion to the axial motion of anvil assembly 30 when knob 50 is rotated. A portion of indicator member 90 is visible through aperture 84 in handle body 80 and has on it a transverse indicator mark or line 94. Another transverse indicator mark 86 is provided on body 80 on each side of aperture 84. Indicator marks 86 and 94 are arranged so that mark 94 coincides with marks 86 when and only when anvil assembly 30 is spaced from staple containing assembly 20 by a distance which allows proper staple formation. Thus the user of the instrument knows that the staples can be fired when mark 94 is observed to coincide with marks 86. The direction of motion of mark 94 relative to marks 86 is also a visible indication of the direction of motion of anvil assembly 30 relative to staple containing assembly 20.

III. Construction and Operation of the Staple Driving Mechanism

As mentioned above, staples 22 and knife 24 are advanced by a self-powering mechanism in assembly 16. This self-powering mechanism is best seen in FIGS. 12–16. The principal element of this mechanism is an initially prestressed compression coil spring 150 which is compressed between annular collar 160 at the proximal end of assembly 16 and a releasable spring retention mechanism 170 at the distal end of assembly 16.

The elements restraining compression spring 150 are best seen initially in FIGS. 12 and 13. Annular collar 160 bears against the end of annular connector 162 which provides a threaded connection between shaft 14 and the tubular outer shell 164 of assembly 16. The other end of spring 150 bears on annular cam follower ring 172 of spring retention mechanism 170 (see also FIGS. 14 and 15). The inner surface of ring 172 has a purality of circumferentially spaced, inwardly projecting longitudinal cam followers 174. As best seen in FIG. 15, the distal end of each of cam followers 174 initially bears on a respective one of inclined cam surfaces 182 on annular cam ring 180 adjacent cam follower stop surfaces 184. Cam ring 180 bears in turn on annular shoulder 192 on annular collar 190 as shown, for example, in FIGS. 12 and 13. The actual construction of collar 190 is better seen in FIGS. 14–18. As shown in those Figures, collar 190 includes concentric inner and outer rings 194 and 196 joined by a plurality of radial spokes 198. Annular surface 192 is on inner ring 194, while (as shown for example in FIG. 12) outer ring 196 bears against inwardly projecting flange 166 near the distal end of shell 164. Accordingly, substantially all of the force exerted by spring 150 prior to release as described below is resisted by the mechanical circuit including collar 160, connector 162, shell 164, collar 190, cam ring 180, and cam follower ring 172. Because the force of spring 150 is used to drive staples 22 and knife 24 as described below, spring 150 is required to exert a relatively large force. For example, the force required to drive the staples may be as much as 300 lbs., and the force required to drive the knife may be of the order of 200 lbs.

In the assembly just described, cam ring 180 is rotatable about the longitudinal axis of the instrument. The slope of cam surfaces 182 is such that spring 150 cannot turn cam ring 180 by itself, but this slope is also such that a relatively small additional rotational force applied to cam ring 180 will cause it to rotate clockwise as viewed in any of FIG. 14–16. Accordingly, when it is desired to release spring 150 to cause it to advance staples 22 and knife 24, a relatively small rotational force is applied to cam ring 180 by operation of control mechanism 60 is described below. In response to this rotational force, cam ring 180 rotates (clockwise as viewed in FIGS. 14–16) from its initial position shown in FIG. 15 to its final position shown in FIG. 16. Cam followers 174 on ring 172 (which does not rotate) follow cam surfaces 182 until reaching axial slots 186 at the end of cam surfaces 182. Can followers 174 then pass through slots 186 as shown in FIG. 16, thereby abruptly completing release of spring 150. When thus reeased, spring 150 drives cam ring 172 axially of the instrument toward staple containing assembly 20.

As shown in FIGS. 14–18, cam follower ring 172 has a plurality of axially extending fingers 176 which pass through apertures 199 between spokes 198 in collar 190 (see especially FIGS. 17 and 18). As is best seen in FIG. 19, prior to release of spring 150, the distal ends 178 of fingers 176 are adjacent axially movable collar 200 in staple containing assembly 20. Collar 200 contacts staple pusher assembly 210 which includes a plurality of staple pushers 212, each of which extends into a respective one of staple containing apertures 222 in staple holder 220. Collar 200 also contacts knife holder 230, to which knife 24 is attached. Collar 200 has a plurality of vent holes 202 extending therethrough to prevent fluid pressure from building up unduly inside staple containing assembly 20 during any phase of the operation of the instrument, and especially during release of spring 150.

When spring 150 is released as described above, spring 150 drives cam follower ring 172 and fingers 176 toward the distal end of the instrument as shown in FIG. 20. The distal ends 178 of fingers 176 contact collar 200 and drive it in the distal direction. Collar 200 in turn drives staple pusher assembly 210 and knife holder 230 in the distal direction. This causes staple pushers 212 to force staples 22 out of holder 220, through the approximated tissue, and against anvil assembly 30 where the staples are crimped to enable them to hold the tissue together. As the staples are being crimped, knife 24 is forced through the excess tissue and against resilient knife anvil 36, thereby cutting through the excess tissue inside the staple array. Knife 24 may also cut through knife anvil 36 (which may be of resilient material) as indicated by cut 236 in FIG. 21. The anastomosis procedure is now complete and the instrument can be removed by operating knob 50 to separate anvil assembly 30 from staple containing assembly 20 as shown in FIG. 21 and withdrawing the instrument from tissue section 40 as described above.

Two features associated with release of spring 150 have not yet been described. If desired, a safety pin 240 can be initially positioned as shown in FIG. 6 to project through shell 164 and into cam ring 180 to prevent the cam ring from turning as required to release spring 150. Accordingly, spring 150 cannot be released until safety pin 240 has been removed. This will normally be done when the instrument is being readied for use. Another desirable feature also visible in FIG. 6 is shock absorbing ring 242 of compressible rubber foam or the like between a portion of cam follower ring 172 and collar 190. As shown in FIG. 20, shock absorbing ring 242 is compressed toward the end of the stroke of cam follower ring 172 after release of spring 150, thereby absorbing a substantial part of the shock which would otherwise occur at the end of the stroke.

The mechanism for applying the relatively small rotational force required to release spring 150 is shown in part in FIG. 4. This mechanism is operated by pivotable control lever 60 which is pivotally mounted on axis 252 through radial projection 254 from hollow shaft 250 inside handle body 80. Control lever 60 is initially positioned parallel to the longitudinal axis of handle 12 as shown in full lines in FIG. 4 (see also FIGS. 1 and 3). When the user of the instrument is ready to release spring 150 and drive the staples, the user pivots control lever 60 outward perpendicular to handle 12 to the second broken line position shown in FIG. 4 (also the solid line position shown in FIG. 2).

A safety interlock is provided between the mechanism for positioning anvil assembly 30 and control lever 60 to prevent the control lever from being pivoted out to the operative position unless the anvil is positioned to provide proper staple formation. This safety interlock is best seen in FIG. 3 and includes fingers 96 projecting forward from anvil position indicator 90 and extending under the rear end 62 of lever 60 unless indicator 90 has been moved proximally a sufficient distance to place indicator mark 94 between indicator marks 86 to indicate that anvil assembly 30 is in position for proper staple formation. As long as fingers 96 extend under the end 62 of lever 60, fingers 96 prevent lever 60 from being pivoted out to its operative position. When indicator mark 94 is aligned between marks 86, however, fingers 96 are withdrawn from beneath lever 60, and lever 60 can be pivoted out for operation.

Returning to FIG. 4, shaft 250 is rotatably mounted in handle body 80. Rotation of shaft 250 is coupled to a further rotatable hollow shaft 260 by longitudinal key and slot interconnection 256. Shaft 260 is coupled to a hollow, flexible, rotatable torque transmission assembly 270 which transmits the rotation of shaft 260 along the length of curved shaft 14 to further elements in assembly 16. Flexible torque transmission assembly 270 is shown in greater detail in FIGS. 7-11. As shown in those Figures, assembly 270 is made up of a plurality of separate toothed rings 280 which are held together in a longitudinal stack or series by an internal tension coil spring 290. Each ring 280 has a plurality of ratchet teeth 282 on each of its opposite faces. The teeth on each ring mesh with the teeth on the adjacent rings and are shaped so that torque is transmitted by the assembly only in the angular direction required to release spring retention mechanism 170. Tension coil spring 290 holds rings 280 together, but also allows the assembly to curve or bend as is required to transmit torque along curved shaft 14. Torque is applied to assembly 270 by teeth 262 on the end of shaft 260, and the torque transmitted by assembly 270 is coupled to the succeeding elements by toothed ring 300. Compression coil spring 264 (FIG. 4) biases shaft 260 and torque transmission assembly 270 distally of the instrument to maintain the engagement of teeth 262 and the teeth on ring 300 with assembly 270. As shown for example in FIG. 13, toothed ring 300 is connected to the proximal end of hollow shaft 310 which is rotatably mounted in assembly 16. Cam ring 180 is mounted on the distal end of shaft 310.

Elements 250, 260, 264, 270, and 300 are all made hollow to accommodate flexible connection 100 which passes coaxially through them.

In operation, when anvil assembly 30 has been properly positioned relative to staple containing assembly 20 (as indicated by the alignment of indicator marks 94 and 86) and it is desired to release spring 150 to drive staples 22 and knife 24, control lever 60 is pivoted out to the position shown in full lines in FIG. 2. From that position lever 60 is rotated clockwise as viewed in FIG. 2 to the dotted line position shown in that Figure. The amount of rotation is somewhat less than 90 degrees. This rotation of control lever 60 causes corresponding rotation of shaft 250, which in turn rotates shaft 260, flexible torque transmission assembly 270, ring 300, shaft 310, and finally cam ring 180. Rotation of cam ring 180 releases spring 150 which then drives staples 22 and knife 24 as described above.

IV. Other Features

Although instrument 10 could be reused by resetting spring 150 and reloading staple containing assembly 20, the instrument is preferably intended to be discarded after a single use, thereby avoiding all difficulty and expense of cleaning and sterilizing between uses. The instrument is particularly suitable to manufacture as a disposable item because most of the instrument is never subjected to any large forces such as those required to approximate and clamp the tissue and drive staples 22 and knife 24. This is because all such large forces operate only in the area of assembly 16, staple containing assembly 20, and anvil assembly 30 and are not transmitted to the remainder of the instrument. Accordingly, while many of the parts in assemblies 16, 20, and 30 may be metal, much of the remainder of the instrument can be of relatively light construction and inexpensive materials such as plastic. This includes most of the parts associated with handle 12 and shaft 14, with the possible exceptions of flexible connection 100 and springs 264 and 290. The overall cost of the instrument can therefore be relatively low. This aspect of the invention is particularly significant with respect to curved shaft 14 which could not withstand large forces along its length without significant deformation (e.g., a change in curvature) unless made of heavy construction and probably of metal. Any significant change in curvature of shaft 14 would of course be unacceptable in an instrument requiring precise and steady positioning during use. Such heavy construction of shaft 14 is not necessary in the instrument of this invention because shaft 14 is not required to carry any large forces.

Although the invention has been illustrated in its application to instruments for performing end-to-end anastomosis of hollow body organs, the invention is equally applicable to other types of surgical fastening instruments and methods, especially those requiring relatively large forces at a location remote from the location at which the instrument is manipulated. For example, the principles of the invention are applicable to other types of surgical stapling instruments such as the thoracic-abdominal surgical staplers shown, for example, in Green U.S. Pat. No. 3,494,533. The invention is also applicable to surgical fastening instruments and methods employing fasteners other than staples, for example, fasteners of the type shown in Noiles U.S. Pat. No. 4,060,089.

It will be understood that the embodiments shown and described herein are merely illustrative of the principles of the invention and that various modifications can be implemented by those skilled in the art without departing from the scope and spirit of the invention. For example, although an instrument with a curved shaft 14 has been shown and described, the shaft could be straight. In that event, relatively inflexible connections could be used in place of flexible connections 100 and 270. Similarly, if the instrument shown and described herein were made reusable, staple containing assembly 20 and anvil assembly 30 could be made as a removable disposable cartridge to facilitate reuse of the instrument.

We claim:

1. A self-powered surgical fastening instrument for performing a surgical fastening procedure at a location remote from the location at which the instrument is manipulated comprising:
   an elongated member having opposite distal and proximal ends;
   means located at the distal end of the elongated member for performing the surgical fastening procedure and including self-powering means for providing the force required to perform at least part of the surgical fastening procedure and further including releasable retention means for retaining the self-powering means in a restrained position and for controlling the release of the self-powering means;
   control means mounted on the proximal end of the elongated member; and
   means located within the elongated member for transmitting control forces between the control means and the releasable retention means so taht the self-powering means is remotely controlled by the control means.

2. The apparatus defined in claim 1 wherein the elongated member is a hollow tube and wherein the means for connecting the control means to the releasable retention means is disposed in the hollow tube.

3. The apparatus defined in claim 2 wherein the releasable retention means is controlled by a rotational motion of one of its parts about the longitudinal axis of the elongated member, and wherein the means for connecting the control means to the releasable retention means comprises a longitudinally flexible connection rotatably mounted in the hollow tube for transmitting a torque from the control means to the releasable retention means.

4. The apparatus defined in claim 3 wherein the tube is longitudinally curved.

5. The apparatus defined in claim 4 wherein the surgical fastening procedure includes driving at least one surgical staple and wherein the self-powering means provides the force required to drive the staple.

6. The apparatus defined in claim 5 wherein the means for performing the surgical fastening procedure further includes an anvil and a staple holder from which the staple is driven and crimped against the anvil, and wherein the apparatus further comprises:
   means located at the distal end of the elongated member for positioning the anvil relative to the staple holder;
   anvil control means mounted on the proximal end of the elongated member; and
   means located within the elongated member for connecting the anvil control means to the means for positioning the anvil so that the means for positioning the anvil is controlled by the anvil control means.

7. The apparatus defined in claim 6 wherein the means for positioning the anvil operates by rotation of one of its parts about the longitudinal axis of the elongated member, and wherein the means for connecting the anvil control means to the means for positioning the anvil comprises a second longitudinally flexible connection rotatably mounted in the hollow tube.

8. The apparatus defined in claim 6 wherein the anvil control means includes means for indicating the position of the anvil relative to the staple holder.

9. The apparatus defined in claim 6 wherein the anvil control means includes means for preventing operation of the control means for the self-powering means unless the anvil is positioned for proper crimping of the staple.

10. The apparatus defined in claim 6 wherein the surgical fastening procedure is anastomosis of hollow body organs using an annular array of surgical staples, and wherein the means for performing the surgical fastening procedure further comprises:
    an annular knife for cutting away excess tissue inside the annular staple array; and
    means operated by the self-powering means for driving the knife to cut away the excess tissue.

11. A surgical instrument for performing anastomosis of hollow tubular body organs comprising:
    an elongated member having opposite distal and proximal ends;
    means mounted on the distal end of the elongated member for first approximating the tissue to be anastomosed and then stapling the approximated tissue together, the staples being driven by self-powering means included in the means mounted on the distal end of the elongated member;
    releasable retention means included in the means mounted on the distal end of the elongated member for controlling the release of the self-powering means and for confining the forces exerted by the self-powering means to the means mounted on the distal end of the elongated member;
    control means mounted on the proximal end of the elongated member; and
    means located within the elongated member for connecting the control means to the releasable retention means so that the self-powering means is remotely controlled by the control means.

12. The apparatus defined in claim 11 wherein the means mounted on the distal end of the elongated member further comprises:
    a staple holder containing a pluralty of staples;
    means coupled to the self-powering means for driving the staples from the staple holder;
    an anvil movable relative to the staple holder for approximating the tissue to be anastomosed between the anvil and the staple holder and for crimping the staples driven from the staple holder; and means for positioning the anvil relative to the staple holder.

13. The apparatus defined in claim 12 wherein the means mounted on the proximal end of the elongated member comprises anvil control means for controlling the means for positioning the anvil.

14. The apparatus defined in claim 13 wherein the anvil control means comprises means for providing a visible indication of the location of the anvil relative to the staple holder.

15. The apparatus defined in claim 13 wherein the means mounted on the proximal end of the elongated member further comprises:
   interlock means for preventing operation of the self-powering control means until the anvil control means has been operated to position the anvil for proper crimping of the staples.

16. The apparatus defined in claim 13 wherein the self-powering means is released to drive the staples by rotation of a part of the releasable retention means relative to the longitudinal member and wherein the control means is connected to the rotatable part of the releasable retention means by a first longitudinally flexible connection capable of transmitting torque.

17. The apparatus defined in claim 16 wherein the means for positioning the anvil operates by rotation of one of its parts relative to the elongated member and wherein the anvil control means is connected to the rotatable part of the means for positioning the anvil by a second longitudinal flexible connection.

18. The apparatus defined in claim 17 wherein the elongated member is a hollow tube and wherein the first and second flexible connections are disposed in the hollow tube.

19. The apparatus defined in claim 18 wherein the elongated member is longitudinally curved.

20. The apparatus defined in claim 13 wherein the self-powering means comprises
   a prestressed spring; and the
   releasable retention means comprises means for maintaining the spring in prestressed condition until released by operation of the control means.

21. A surgical instrument for performing anastomosis of hollow tubular body organs comprising:
   (A) an elongated member having opposite distal and proximal ends;
   (B) first means mounted on the distal end of the elongated member for first approximating the tissue to be anastomosed and then stapling the approximated tissue together, the first means including (1) a staple holder containing a plurality of staples, (2) self-powering means comprising a prestressed coil spring for driving the staples from the staple holder, (3) an anvil movable relative to the staple holder for approximating the tissue to be anastomosed between the anvil and the staple holder and for crimping the staples driven from the staple holder, (4) means for positioning the anvil relative to the staple holder, and (5) releasable retention means comprising means for (a) maintaining the spring in prestressed condition, (b) controlling the release of the self-powering means, and (c) confining the forces exerted by the self-powering means to the first means;
   (C) control means mounted on the proximal end of the elongated member and including anvil control means for controlling the means for positioning the anvil; and
   (D) means located within the elongated member for connecting the control means to the releasable retention means so that the self-powering means is remotely controlled by the control means;
   (E) the releasable retention means further comprising (1) a cam ring having a plurality of circumferentially extending cam surfaces, and (2) a cam follower ring having a plurality of circumferentially extending cam follower surfaces, each of which contacts a respective one of the cam surfaces, one of the cam ring and cam follower ring being connected to one end of the spring, the cam ring and cam follower ring being rotatable relative to one another so that the cam followers move along their respective cam surfaces, and the cam surfaces being inclined in the direction of movement of the cam followers so that movement of the cam followers tends to release the spring and so that only a relatively small force applied by the control means is required to move the cam followers relative to the cam surfaces to release the spring.

22. The apparatus defined in claim 21 wherein the cam surfaces are circumferentially spaced so that the cam followers abruptly leave the cam surfaces after a predetermined motion to abruptly complete release of the spring.

23. The apparatus defined in claim 13 wherein the means mounted on the distal end of the elongated member further comprises:
   a knife; and
   means coupled to the self-powering means for driving the knife against the anvil to cut away excess tissue.

24. The apparatus defined in claim 23 wherein a plurality of staples is driven simultaneously in an annular array and wherein the knife is annular and concentric with the annular staple array.

* * * * *